United States Patent
Hrboticka (12)

(10) Patent No.: US 10,246,732 B2
(45) Date of Patent: Apr. 2, 2019

(54) STABILIZED TEST STRIP FOR THE DETECTION OF HYDROGEN PEROXIDE

(71) Applicant: Precision Laboratories, Inc., Cottonwood, AZ (US)

(72) Inventor: Eva Hrboticka, Brno (CZ)

(73) Assignee: PRECISION LABORATORIES, INC., Cottonwood, AZ (US)

( * ) Notice: Subject to any disclaimer, the term of this patent is extended or adjusted under 35 U.S.C. 154(b) by 123 days.

(21) Appl. No.: 15/340,229

(22) Filed: Nov. 1, 2016

(65) Prior Publication Data

US 2018/0119197 A1     May 3, 2018

(51) Int. Cl.
| | |
|---|---|
| *C12Q 1/28* | (2006.01) |
| *G01N 21/78* | (2006.01) |
| *G01N 33/22* | (2006.01) |
| *G01N 33/52* | (2006.01) |
| *G01N 21/77* | (2006.01) |

(52) U.S. Cl.
CPC ........ *C12Q 1/28* (2013.01); *C12Y 111/01007* (2013.01); *G01N 21/78* (2013.01); *G01N 33/227* (2013.01); *G01N 33/52* (2013.01); *G01N 2021/7759* (2013.01); *G01N 2333/908* (2013.01)

(58) Field of Classification Search
None
See application file for complete search history.

(56) References Cited

U.S. PATENT DOCUMENTS

| | | | | |
|---|---|---|---|---|
| 5,620,863 | A * | 4/1997 | Tomasco | C12Q 1/54 422/422 |
| 9,714,939 | B1 * | 7/2017 | Zhang | G01N 33/52 |
| 2004/0171087 | A1 * | 9/2004 | Rech-Weichselbraun | G01N 33/54353 435/7.5 |
| 2015/0072435 | A1 * | 3/2015 | Hrboticka | G01N 21/78 436/135 |

OTHER PUBLICATIONS

Vujcic et al., "Exploitation of neglected horseradish peroxidase izoenzymes for dye decolorization", International Biodeterioration & Biodegradation, vol. 97, pp. 124-127. (Year: 2015).*

* cited by examiner

*Primary Examiner* — Michelle F. Paguio Frising
(74) *Attorney, Agent, or Firm* — Ladas & Parry LLP

(57) ABSTRACT

A colorimetric dry-reagent test strip for direct detection of the presence of hydrogen peroxide in strongly acidic solutions without the necessity of a pH neutralization step comprises a chromogen responsive to hydrogen peroxide, an enzyme peroxidase catalyst and at least one complexing agent chosen to protect an active site of the catalyst for an amount of time sufficient to allow for the catalytic oxidation of the chromogen. The test strip has particular value in the determination of peroxide-based explosive compounds, such as hexamethylene triperoxide diamine (HMTD) or triacetone triperoxide (TATP), which require a treatment with a strong organic acid to release the hydrogen peroxide to be detected, and typically requires neutralization of the acid before a conventional test strip can be employed. The invention dispenses with the need for such a neutralization step.

10 Claims, 1 Drawing Sheet

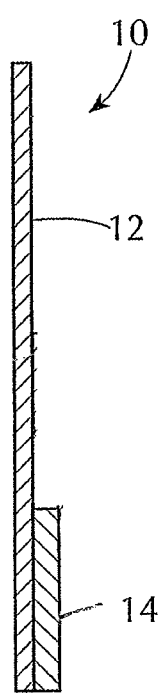

STABILIZED TEST STRIP FOR THE DETECTION OF HYDROGEN PEROXIDE

FIELD OF THE INVENTION

The present invention relates to an improved and stabilized test strip for direct detection of hydrogen peroxide in a strongly acidic medium without necessity of a neutralization step. More particularly, the present invention relates to a test strip for fast and simple detection of peroxide based explosives.

BACKGROUND OF THE INVENTION AND PRIOR ART

Colorimetric dry reagent test strips, also called "dipsticks" or "dip-and-read reagent strips" are widely used for analyses, particularly outside a laboratory, where there is a necessity for a fast and simple detection.

Test strips for detection of hydrogen peroxide appeared on the market decades ago as a secondary (standby) product of sophisticated multi-enzymatic dry reagent test strips used in clinical chemistry for analyses of pathologically significant substances (enzymatic substrates) in body fluids, such as the analysis of glucose, uric acid, cholesterol etc. The principle underlying these test strips is that a corresponding oxidase enzyme converts a substrate into a particular reaction product while releasing hydrogen peroxide, which in following steps is the subject of a colorimetric detection to confirm the presence of the reaction product. Subsequently the market recognized that similar chemistry could be used for the sensing and determination of hydrogen peroxide, per se.

Broadly, these test strips comprise a plastic strip, at one end of which is mounted an absorbent portion impregnated with the appropriate reactant mixture. The test strips are used by dipping the reactant-bearing end into the test sample, removing it and evaluating the color formed in the paper portion.

Typically, the absorbent portion of such test strip includes an bibulous absorbent material, such as a cellulosic material, carrying a reactant composition capable of the color reaction with the compound the interest, namely hydrogen peroxide, generated from the analyzed sample. Such reactant compositions comprise an enzyme peroxidase or peroxidase-like substance and a chromogen compound capable of forming color or changing color in the presence of hydrogen peroxide. When this reactant system contained in the test strip comes into the contact with hydrogen peroxide, the peroxidase catalyzes a reaction between the hydrogen peroxide and the color changing compound to produce an oxidized (colored) form of the compound. The visually detectable change of color indicates a positive result.

Without catalysis the oxidation of a chromogen by hydrogen peroxide is not possible or is so weak that analytical use is not possible. It has been estimated that the presence of a peroxidase or peroxidase-like compound as a catalyst increases the sensitivity of detection over a thousandfold. For that reason the catalytic agent plays crucial role in detection of hydrogen peroxide, especially in low concentrations.

Substances having peroxidase activity include the vegetable peroxidases, such as horseradish, turnip, soybean or potato peroxidase; further inorganic compounds such as iodide and molybdate salts, iron thiocyanate, iron tannate etc. Red blood cells, urohemin and other porphyrin substances also have peroxidase activity, as do other compounds or combinations of compounds (see e.g. U.S. Pat. Nos. 3,298,789; 2,981,606; and 4,361,648). Some inorganic salts with peroxidase-like activity provide, in comparison with enzyme peroxidase, a much lower activity, resulting in significantly lower sensitivity of the analysis, especially in methods where a quick result is important. Since test strips, in general, are intended to offer a fast analysis, in the order of seconds, the use of a peroxidase enzyme for catalysis is crucial and thus are preferred in tests where high sensitivity and fast result are requested.

Enzyme activity and stability are generally strictly limited by pH. The most suitable peroxidases for analytical devices are horseradish peroxidases; their optimal pH range is about 6.0-6.5 pH units and their pH stability range is between 5.0 to 10.0 pH units. Other peroxidase compositions are set forth, for example, in U.S. Pat. Nos. 2,981,606; 3,012,976; 3,335,069; 3,558,435; 3,627,698; 4,361,648; 4,427,770; EP 0 217 246; EP 0 268 167.

The peroxidase catalyzes the reaction between hydrogen peroxide and the chromogen/color changing compound to produce the oxidized form of the compound. The color changing compound can be any compound capable of producing a color in the contact with hydrogen peroxide and enzyme peroxidase or generally a substance having peroxidase activity, and can be divided into two basic groups, leuco dye type chromogens, which are oxidized to form color products; and coupling type chromogens, which are oxidized to colorless compounds and coupled with a suitable coupler to form a final color product. A reactant composition incorporating a chromogen can preferably also contain non-reactive supportive compounds, such as buffer, polymers and wetting agents to improve the test strip's properties.

Colorimetric test strips provide a suitable analytical tool, especially in so-called field analyses, where there is a need for simple, fast and sensitive tests. Test strips contain all the reagents necessary for the test on single test pad in dry form, which also provides an advantage in the transportation of the strips and makes testing fast and easy, even for people not skilled in analytical techniques. Moreover no attendant apparatus is required. Thus, peroxide test strips can be a suitable analytical tool for the field detection of organic peroxide explosives, such as triaceton triperoxide (TATP) and hexamethylene triperoxide diamine (HMTD), often used in home-made explosives in terrorists attacks. The obstacle against use of commercially available peroxide test strips for that purpose is the use of strong mineral acids for the needed degradation of a peroxide-based explosive to release hydrogen peroxide. Such an acid degradation reaction, also called an acid treatment, is a broadly used procedure for releasing the detectable analyte (hydrogen peroxide) from rigid organic molecules in various testing methods, such as fluorescent, chemiluminescent, electrochemical and spectrophotometric detections (see, e.g. Anal. Bioanal. Chem. (2011) 400:313-320; Inorg. Chem. (2008) 47:9748-50; Analyst (2010) 135:2085-91; and Talanta (2015) 143:191-197).

Strong mineral acids, such as sulfuric and hydrochloric acid, are most often used for the needed acid degradation of peroxide based organic molecules; e.g. HCl in concentrations of 6N up to 32%. Such acid treatments result in a pH of the mixture in the range 0-1 pH units. The dipping of a test strip directly into such an acidic sample mixture would destroy the enzyme immediately, resulting in complete loss of its catalytic activity. Since a peroxidase enzyme is readily and irreversibly deactivated under strong acidic conditions, an additional procedure step is always required to neutralize the acidic mixture and adjust its pH to a value where the enzyme would be able to catalyze the needed interaction between hydrogen peroxide and chromogen, which is in the range of 5-9 pH units.

Such procedures are currently performed in laboratory methods and analytical kits (e.g. as set forth in U.S. Pat. No. 6,767,717) which require neutralization before a peroxidase can be introduced into the test mixture, but for dry-reagent test strip application, where the priority is for a fast and simple field test, (literally a "pocket-test"), which can be used by non-experts, the need for such additional neutralization step is a serious drawback.

SUMMARY OF THE INVENTION

It is the object of the present invention to provide a test strip (dipstick) for fast, simple and sensitive detection of hydrogen peroxide released from peroxide-based explosives directly in the acidic mixture resulting from the required acid treatment without the necessity to neutralize and adjust pH. It is thus the object of the present invention to avoid the instant, total and irreversible loss of catalytic activity of a peroxidase enzyme against hydrogen peroxide which normally results from contact with a strong acidic medium (pH 0-1), by providing a stabilized and protected enzyme peroxidase to keep its necessary catalytic reaction activity for fast and sensitive detection of hydrogen peroxide under such a strong acidic condition.

More particularly, the present invention is directed to a dry reagent test strip (dipstick or dipstrip) in which all components, including a peroxidase enzyme, are carried in one piece of absorbent material, wherein the peroxidase enzyme is protected to maintain its catalytic activity in strong acidic mediums having a pH from 0-1.

The present invention is based on the surprising discovery that the treatment of a peroxidase enzyme with one or more complexing agents provides efficient protection of the enzyme's active site for a period of time, which can be long enough to allow for the catalytic oxidation of a chromogenic substrate by hydrogen peroxide in a strongly acidic solution with pH about 0. Suitable peroxidases for such treatment include nonspecific peroxidases derived from vegetable sources, among them being horseradish peroxidase, which contains both, acidic and basic isoenzymes, which is preferred. The complexing agents are chosen from polycarboxylic and polyaminopolycarboxylic compounds.

BRIEF DESCRIPTION OF THE DRAWING

FIG. 1 is a representation of a handled dipstick or dipstrip embodying the present invention.

DETAILED DESCRIPTION OF THE INVENTION

Prior attempts for enzyme stabilization were directed to preserving enzyme activity by preventing enzyme decomposition during storage. For example, U.S. Pat. No. 4,283,491 and EP 0 252 750 disclose the use of polymers to improve storage time. Upon realizing that none of the described and applied methods would achieve the type of enzyme protection desired in a peroxide test strip in strong acidic conditions, it was recognized that a different tack was necessary—a focus on the enzyme's molecular structure and the mechanism of its catalytic activity.

Horseradish peroxidase and other vegetable and plant peroxidases, such as soybeen, turnip, barley, tomato and tobacco peroxidases, are class III peroxidases. They contain an N-terminal peptide, two calcium ions, four disulfide bridges and an extra helical region that plays a role in an access to the edge of the heme cofactor present in the peroxidase.

Horseradish peroxidase (HRP) is a heme protein with 308 amino acids residues. The N-terminal residue is blocked by a pyrrolidennecarboxyl residue which appears to be buried inside the polypeptide chain. The heme prosthetic group is ferriprotoporphyrin, which is made of four pyrrole rings joined by methene bridges with iron (III) in the center of the molecule. Three different substitutes are found in the pyrrole rings—four methyl, two vinyl and two propionate side chains.

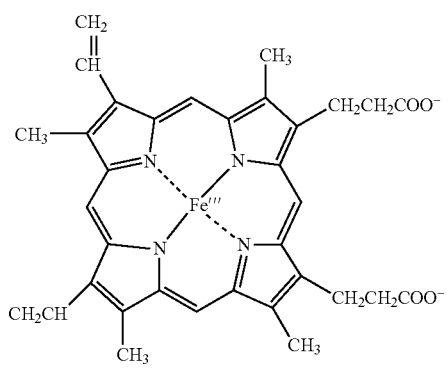

The activity of enzymes is strongly affected by changes in pH. This is due to the importance of the tertiary structure in the enzyme function and forces, e.g. ionic interactions and hydrogen bridges, in determining the shape of the enzyme molecule. Changes in pH alter the state of ionization of charged amino acids that may play a crucial role in substrate binding and/or catalytic action itself. For enzymatic activity to occur there needs to be a certain degree of conformational flexibility in the enzyme structure, enabling entry of the substrate into the active site and attainment of the transition state structure, where there is a delicate balance between hydrophobic interactions, charge interaction and hydrogen bridges. Changes in pH can break the hydrogen bridges and hydrophobic interactions in the enzyme structure of peroxidase, allowing the rapid unfolding and inactivation of the enzyme. Thus an approach to stabilizing enzyme activity would be the introduction of molecules with the proper polar groups and steric arrangement to negate the effect of pH changes on the enzymatic activity of the peroxidase.

Accordingly, It has been found that complexing a peroxidase with one or more polycarboxylic or polyaminocarboxylic compounds stabilizes the enzyme sufficiently in a highly acidic condition to allow it to catalyze the needed chromogen oxidation for peroxide identification.

Of these complexing agents, compounds with three to six carboxylic groups have been found to be particularly suitable for proper protection of the HRP active site in such acidic mediums; these include N-(2-hydroxyethyl)ethylenediamine triacetate; 1,2,3-propanetricarboxylic anion; triglycine; ethylenedinitrilotetraacetate; ethylene glycol-bis(β-aminoethyl ether) tetraacetate; cyclohexylenedinitrilotetraacetate; diethylene-triaminepentaacetate; and triethylenetetraaminehexaacetate.

More efficient enzyme protection at pH 0-1 has been observed when a combination of complexing agents, each with three and four carboxylic groups, was used in a concentration appropriate to the peroxidase activity unit (POD Unit), which is that amount of enzyme decomposing 1 μmole of peroxide/minute at 25° C.

Although the specific mode of action providing the novel peroxidase protection and stabilization is not fully understood, the complexing agent treatment brings protection against strong acidic ambient conditions. Another advantage resulting from the treatment is an improved stability of the enzyme during storage and thus prolongation of test strip shelf life.

FIG. 1 depicts a peroxide "dip and read" test strip 10 of the invention utilizing an appropriate support or wand. Carrier matrix 14 is advantageously affixed to insoluble support 12 for easy manipulation. Broadly, such a support may comprise a plastic wand, at one end of which is mounted the carrier matrix, an absorbent material test strip impregnated with the appropriate reactant mixture. The term "carrier matrix" refers to bibulous or nonbibulous materials which are absorbent and maintain their structural integrity when exposed to liquids. Such materials are known in the art. The carrier matrix is initially immersed in, soaked, sprayed or printed with the reactant composition, and thereafter dried by suitable means, such as by ambient or forced air drying, to leave the dry reagent material suspended in the carrier matrix (e.g. paper). The resultant test strip material (typically in squares 5×5 mm) is then affixed to the support for easy manipulation. Alternatively, the carrier matrix may be first affixed to the wand and thereafter soaked with the reactant composition and allowed to dry. The wand is used by dipping the end bearing the test strip into the test sample, removing it and evaluating the color formed in the paper portion. This type of technology is well known in the art.

The test strip of the present invention is well suited for the field determination and detection of the presence of peroxide-based explosive compounds, such as hexamethylene triperoxide diamine (HMTD) or triacetone triperoxide (TATP), which release hydrogen peroxide after an acidic degradation treatment. For such use, it is necessary to at least partially dissolve the HMTD or TATP. Such solvents may include methanol and ethanol. Such a field kit may thus include a dropper vial of solvent, a dropper vial of a strong mineral acid to degrade the explosive, a vial into which the sample is placed and into which the solvent and acid can be added, and a test strip for dipping into the dissolved and degraded sample solution for determination and subsequent color-change observation.

Typical reactant compositions for peroxide test strips in accordance with the present invention may contain, in addition to the chromogen, enzyme peroxidase, and complexing agent for the peroxidase, a buffer, a polymer and a wetting agent, as well known in the art for similar strips. The following examples illustrate that conventional test strip formulations demonstrate no reactivity in a solution of hydrogen peroxide where solution acidity was adjusted with hydrochloric acid to a pH 2 or lower.

EXAMPLES

The following examples of this inventive method are presented by way of illustration and not of limitation.

Examples I-III

Experiments were performed to compare the reactivity of two sets of peroxide test strips; one prepared in as representing conventional test strip formulation, (the control test strip) and the other with the inventive peroxidase treatment (test strips I, II and III). Both sets of test strips contained the same reactant composition of indicator, peroxidase, buffer, polymer, and wetting agent. The chromogen indicator utilized provides a blue color after the oxidation by hydrogen peroxide. Horseradish peroxidase was used as the catalyst, containing both acidic and basic isoenzymes.

Test strip I contained as a complexing agent penta(carboxymethyl) diethylenetriamine (penta-anion $DTPA^{5-}$) in a concentration of 9 μmol per POD Unit.

Test strip II contained as a complexing agent ethylene glycol-bis(β-aminoethyl ether) tetraacetic anion in a concentration of 5 μmol per POD Unit and 2-hydroxy-1,2,3-popane tricarboxylic anion in a concentration of 8 μmol per POD unit.

Test strip III contained as a complexing agent triglycine in a concentration of 3 μmol per POD unit; ethylenedinitrilotetraacetic anion in a concentration of 3 μmol per POD unit; and β-carboxyglutaric anion in a concentration of 5 μmol per POD unit.

Both the control and test strips were prepared in the same conventional manner as well known in the art using paper as a reactant carrier material. The reactivity of the control and test strips was tested on hydrogen peroxide solutions where acidity was adjusted with 6M hydrochloric acid to values about 0 and 1 pH. The hydrogen peroxide in the solutions was at 20 ppm and 5 ppm levels. The strips were dipped into the solutions for approximately one second. The color of the test pad was evaluated both instantly and within 2 minutes after dipping.

The results of the tests are presented in the following table.

| Test strips | pH~0 | | pH~1 | |
|---|---|---|---|---|
| | 20 ppm | 5 ppm | 20 ppm | 5 ppm |
| Control test strips | No color | No color | No color | No color |
| Example I test strips | Dark Blue | Blue | Dark Blue | Blue |
| Example II test strips | Dark Blue | Blue | Dark Blue | Blue |
| Example III test strips | Dark Blue | Blue | Dark Blue | Blue |

The results confirm that the test strips with the complexing agents provided clear confirmation of the presence of hydrogen peroxide at both pH levels while conventional strips provided no indication whatsoever.

Example IV

An experiment was conducted to determine the improvement in hydrogen peroxide detection by the present invention over conventionally-available peroxidase peroxide test strips. Three commercially available peroxide test strips, each from a different manufacturer (TS1, TS2, TS3) were tested together with peroxide test strips formulated in accordance with the present invention (EX) on acidified hydrogen peroxide solutions—100 ppm solutions of hydrogen peroxide acidified to pH ~0 and ~1.

All strips were dipped into a testing solution for approximately one second. The color reaction was evaluated instantly (and in the case of a negative result also for 2 minutes after dipping).

The results of the tests are presented in the following table.

| Peroxide Test Strips | pH~0 | pH~1 |
|---|---|---|
| TS1 | Negative (no color)* | Negative (no color)* |
| TS2 | Negative (no color)* | Negative (no color)* |
| TS3 | Negative (no color)* | Negative (no color)* |
| EX | Positive (dark blue color) | Positive (dark blue color) |

*No color development was observed during 2 minutes.

Example V

An experiment was performed to determine the sensitivity of peroxide detection of the present invention in a strong acidic solution of pH ~0. A hydrogen peroxide acidified solution was gradually diluted down and the diluted solutions were tested with the inventive test strips (EX) up to last clear positive color reaction. It was found that test strip is able to detect by a noticeable color change within a few seconds the a quantity as small as 0.5 microgram $H_2O_2$.

Example VI

An experiment was performed to demonstrate the potential application of the present invention in the detection of peroxide-based explosive compounds, such as hexamethylene triperoxide diamine (HMTD) or triacetone triperoxide (TATP), which release hydrogen peroxide after an acidic degradation treatment. For such use, it is necessary to at least partially dissolve the HMTD or TATP. Such solvents may include methanol and ethanol. Accordingly, on a virtually imperceptible sample of TATP (without residual hydrogen peroxide) in a vial were dropped methanol (to dissolve the TATP) and 6M hydrochloric acid, followed immediately by a test strip dip. A dark blue color was observed within a few seconds, indicating the presence of hydrogen peroxide. The same results were achieved with a HMTD sample.

A further experiment was carried out to test the potential application in the trace detection of the same compounds. A plain paper sampling strip was used to "swipe" a trace amount of a sample. One drop of methanol from a dropping bottle, followed by one drop of hydrochloric acid, was applied to the sampling strip. The sampling strip was immediately touched with a test strip, resulting in an instant color reaction indicating a positive reaction.

I claim:

1. A colorimetric dry-reagent test strip for direct detection of the presence of hydrogen peroxide in strongly acidic solutions without the necessity of a neutralization step, consisting essentially of a chromogen responsive to hydrogen peroxide, an enzyme peroxidase catalyst and at least one complexing agent at a concentration that effectively protects an active site of the catalyst for an amount of time sufficient to allow for the catalytic oxidation of the chromogen when contacted with hydrogen peroxide-containing solutions having a pH in the range of 0 to 1, wherein the components are in a dry form on a carrier.

2. The test strip of claim 1, wherein the enzyme peroxidase catalyst is horseradish peroxidase having both acidic and basic isoenzymes.

3. The test strip of claim 1, wherein the at least one complexing agent is chosen from the group consisting of polycarboxylic and polyaminopolycarboxylic compounds.

4. The test strip of claim 3, wherein the polycarboxylic and polyaminopolycarboxylic compounds have three to six carboxylic groups.

5. The test strip of claim 1 including two complexing agents.

6. The test strip of claim 1 wherein the dry form components are located in a carrier matrix.

7. The test strip of claim 6 wherein the carrier matrix is mounted to a support.

8. A test kit for detecting a peroxide-based explosive compound, comprising the test strip of claim 1, a solvent for the explosive compound and a mineral acid of pH 0-1 for the degradation of the explosive compound to release hydrogen peroxide.

9. The test kit of claim 8 further including a vial for receiving a sample of the explosive compound to be tested, the solvent and the mineral acid, the test strip being constructed and dimensioned to be insertable into the vial.

10. The test kit of claim 9 wherein the test strip is mounted to a supporting handle.

* * * * *